United States Patent [19]

Tripier et al.

[11] Patent Number: 5,322,926

[45] Date of Patent: Jun. 21, 1994

[54] ISOHIRUDINS

[75] Inventors: Dominique Tripier, Eppstein/Taunus; Peter Crause, Offenbach; Paul Habermann, Eppstein/Taunus; Martin Kramer, Wiesbaden; Joachim Engels, Kronberg/Taunus; Matthias Scharf, Frankfurt am Main, all of Fed. Rep. of Germany

[73] Assignee: Hoechst Aktiengesellschaft, Frankfurt am Main, Fed. Rep. of Germany

[21] Appl. No.: 35,498

[22] Filed: Mar. 22, 1993

Related U.S. Application Data

[63] Continuation of Ser. No. 424,334, Oct. 19, 1989, abandoned.

[30] Foreign Application Priority Data

Oct. 21, 1988 [DE]  Fed. Rep. of Germany ....... 3835815

[51] Int. Cl.$^5$ .................... A61K 37/00; A61K 37/02; C07K 5/00; C07K 7/00
[52] U.S. Cl. .................................................. 530/324
[58] Field of Search .................... 514/12, 822; 530/324

[56] References Cited

U.S. PATENT DOCUMENTS

| | | | |
|---|---|---|---|
| 4,668,662 | 5/1987 | Tripier | 514/12 |
| 4,791,100 | 12/1988 | Kramer et al. | 514/12 |

FOREIGN PATENT DOCUMENTS

| | | |
|---|---|---|
| 41364/85 | 10/1985 | Australia . |
| 43655/85 | 12/1985 | Australia . |
| 45977/85 | 2/1986 | Australia . |
| 60233/86 | 1/1987 | Australia . |
| 65693/86 | 6/1987 | Australia . |
| 18284/88 | 8/1989 | Australia . |
| 73680/91 | 10/1991 | Australia . |
| 1239606 | 7/1988 | Canada . |
| 0142860B1 | 5/1985 | European Pat. Off. . |
| 0142860 | 5/1985 | European Pat. Off. ........ C07K 7/10 |
| 0158986A2 | 10/1985 | European Pat. Off. . |
| 0207956B1 | 12/1985 | European Pat. Off. . |
| 0168342B1 | 1/1986 | European Pat. Off. . |
| 0171024B1 | 2/1986 | European Pat. Off. . |
| 0193175A2 | 9/1986 | European Pat. Off. . |
| 0158564B1 | 10/1986 | European Pat. Off. . |
| 0200655A1 | 11/1986 | European Pat. Off. . |
| 0209061 | 1/1987 | European Pat. Off. ........ C07K 7/10 |
| 0209061A3 | 1/1987 | European Pat. Off. . |
| 0227938B1 | 7/1987 | European Pat. Off. . |
| 0332523 | 3/1989 | European Pat. Off. ...... C12N 15/00 |
| 0316650A3 | 5/1989 | European Pat. Off. . |
| 0324712A3 | 7/1989 | European Pat. Off. . |
| 0448093A3 | 9/1991 | European Pat. Off. . |
| WO85/04418 | 10/1985 | PCT Int'l Appl. . |
| WO86/06406 | 11/1986 | PCT Int'l Appl. . |

OTHER PUBLICATIONS

Smith et al., *Principles of Biochemistry*, 7th Ed., McGraw-Hill, New York, 1983.
Dodt et al., FEBS Letters, vol. 165, No. 2, pp. 180–184, Jan. 1984.
Dodt et al., FEBS Letters, vol. 229, No. 1, pp. 87–90, Feb. 1988.
Geiger et al., "Deamidation, Isomerization, and Racemization at Asparaginyl and Aspartyl Residues in Peptides," Journal of Biological Chemistry, vol. 262, No. 2, 1987, pp. 785–794.
Stephenson et al., "Succinimide Formation from Aspartyl and Asparaginyl Peptides as a Model for the Spontaneous Degradation of Proteins," Journal of Biological Chemistry, vol. 264, No. 11, 1989, pp. 6164–6170.
Bowie et al., "Deciphering the Message in Protein Sequences: Tolerance to Amino Acid Substitutions," Science, vol. 247, Mar. 16, 1990, pp. 1306–1310.
Baskova et al., "Hirudin From Leech Heads and Whole Leaches and 'Pseudo-Hirudin' From Leech Bodies," Thrombosis Research, vol. 30, 1983, pp. 459–467.
Harvey et al., "Cloning and Expression of a cDNA Coding for the Anticoagulant Hirudin From the Bloodsucking Leech, Hirudo medicinalis," Proc. Natl. Acad. Sci. USA, vol. 83, Feb. 1986, pp. 1084–1088.

*Primary Examiner*—Merrell C. Cashion, Jr.
*Assistant Examiner*—A. M. Davenport
*Attorney, Agent, or Firm*—Finnegan, Henderson, Farabow, Garrett & Dunner

[57] ABSTRACT

Thrombin inhibitors from the hirudin family which differ from the previously known hirudins by mutation in the protein chain, and a process for their preparation are described. The novel hirudins are distinguished by a high specific activity, high stability and good pharmacokinetics.

12 Claims, 1 Drawing Sheet

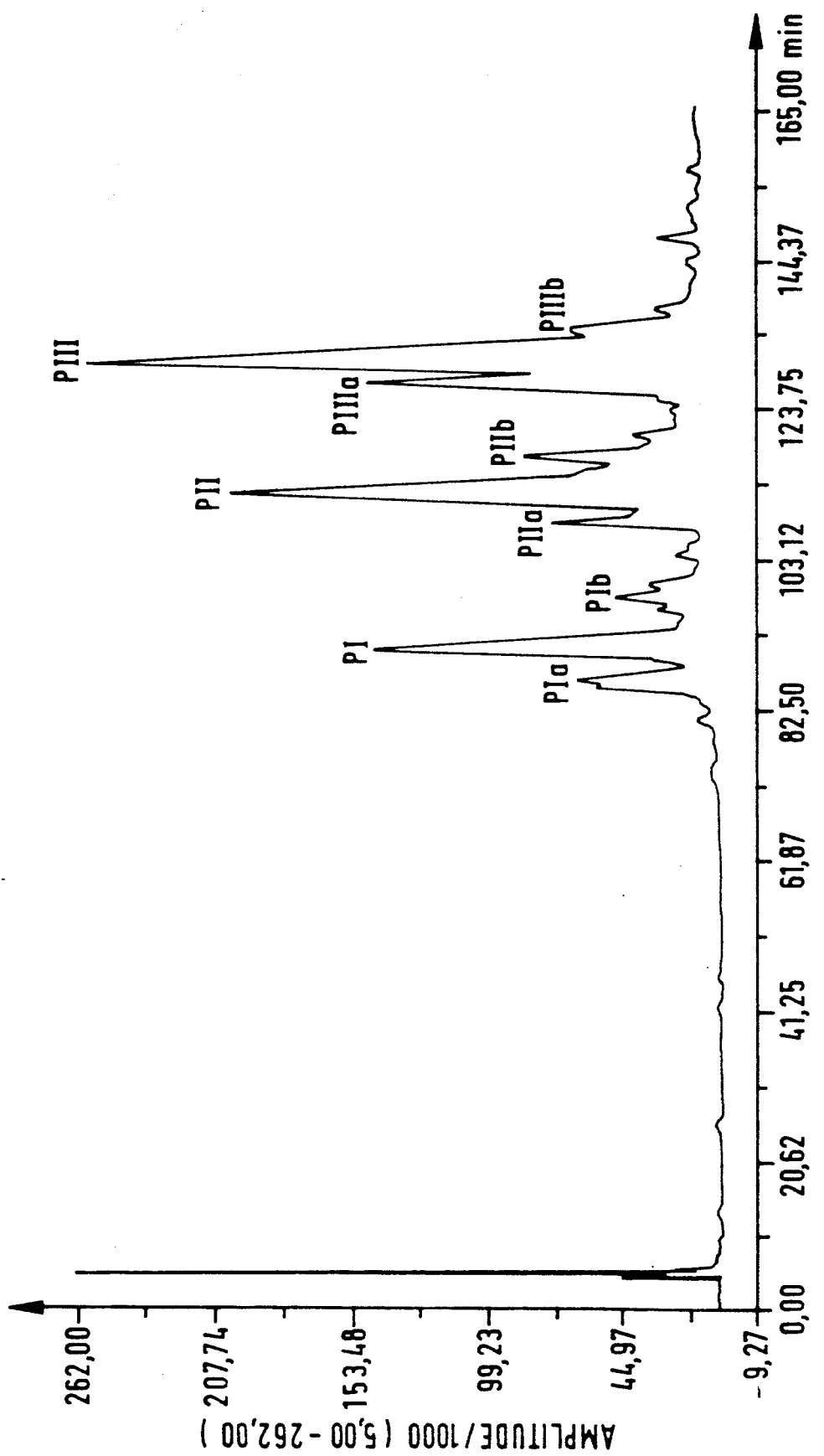

ISOHIRUDINS

This application is a continuation of application Ser. No. 07/424,334, filed Oct. 19, 1989, and now abandoned.

DESCRIPTION

The invention relates to novel thrombin inhibitors from the hirudin family which differ from the previously known hirudins on account of mutation in the protein chain.

Hirudins are known, for example, from EP-A 142,860; EP-A 158,564; EP-A 158,986; EP-A 168,342; EP-A 171,024; EP-A 193,175; EP-A 200,655; EP-A 209,061; EP-A 227,938; Chang, FEBS, Vol. 164 (1983) 307; J. Dodt et al., Biol. Chem. Hoppe-Seyler 367 (1986) 803-811 and D. Tripier, Folia Haematol. Leipzig 115 (1988) 1-2, 30-35. However, these hirudins may be partially bonded via active centers to carriers or via amino acids which participate in the bonding to thrombin. In addition, the known hirudins have limited transdermal properties and are very short-lived for reasons of high elimination rates so that stationary or ambulant thrombosis prophylaxis is made difficult.

The aim is therefore to find hirudins having high specific activity, high stability and good pharmacokinetics. In addition, these hirudins should be distinguished by better chemical manageability on immobilization on carriers.

This aim is achieved according to the invention by the isohirudins of the formula (A)

$$\begin{array}{c}
1 \quad\quad\quad\quad\quad 5 \quad\quad\quad\quad\quad 10 \\
A-B-Tyr-Thr-Asp-Cys-Thr-Glu-Ser-Gly- \\
\\
15 \quad\quad\quad\quad\quad 20 \\
C-E-Leu-Cys-Leu-Cys-F-G-Ser-I-Val- \\
\\
25 \quad\quad\quad\quad\quad 30 \\
Cys-Gly-J-Gly-Asn-Lys-Cys-K-Leu-Gly- \\
\\
35 \quad\quad\quad\quad\quad 40 \\
Ser-L-Gly-Glu-M-Asn-N-Cys-Val-Thr-Gly- \\
\\
45 \quad\quad\quad\quad\quad 50 \\
Glu-Gly-Thr-Pro-Lys-Pro-Gln-Ser-His-Asn- \\
\\
55 \quad\quad\quad\quad\quad 60 \\
Asp-Gly-Asp-Phe-Glu-Glu-Ile-Pro-Glu-Glu- \\
\\
65 \\
Tyr(R)-Leu-Gln
\end{array} \quad (A)$$

in which

A denotes Val or Ile,
B denotes Val or Thr,
C denotes Gln or Glu,
E denotes Asn or Asp,
F denotes Glu or Gln,
G denotes Asp or Gly,
I denotes Asp or Asn,
J denotes Gln, Glu, Asn or Lys,
K denotes Ile or Lys,
L denotes Asp or Asn,
M denotes Lys or Glu,
N denotes Gln or Glu and
R denotes hydrogen or SO₃H, with the proviso that if J stands for Gln, L is not Asp, and their mutants and their physiologically tolerable salts, if such can be formed.

The following isohirudins may be mentioned in particular, where R denotes hydrogen or SO₃H:

Val—Val—Tyr—Thr—Asp—Cys—Thr—Glu—Ser— (Ia)
Gly—Gln—Asn—Leu—Cys—Leu—Cys—Glu—Gly—
Ser—Asn—Val—Cys—Gly—Lys—Gly—Asn—Lys—
Cys—Ile—Leu—Gly—Ser—Asp—Gly—Glu—Lys—
Asn—Gln—Cys—Val—Thr—Gly—Glu—Gly—Thr—
Pro—Lys—Pro—Gln—Ser—His—Asn—Asp—Gly—
Asp—Phe—Glu—Glu—Ile—Pro—Glu—Glu—Tyr(R)—
Leu—Gln

Val—Val—Tyr—Thr—Asp—Cys—Thr—Glu—Ser— (I)
Gly—Gln—Asn—Leu—Cys—Leu—Cys—Glu—Gly—
Ser—Asn—Val—Cys—Gly—Asn—Gly—Asn—Lys—
Cys—Ile—Leu—Gly—Ser—Asp—Gly—Glu—Lys—
Asn—Gln—Cys—Val—Thr—Gly—Glu—Gly—Thr—
Pro—Lys—Pro—Gln—Ser—His—Asn—Asp—Gly—
Asp—Phe—Glu—Glu—Ile—Pro—Glu—Glu—Tyr(R)—
Leu—Gln

Ile—Thr—Tyr—Thr—Asp—Cys—Thr—Glu—Ser— (IIa)
Gly—Gln—Asn—Leu—Cys—Leu—Cys—Glu—Gly—
Ser—Asn—Val—Cys—Gly—Asn—Gly—Asn—Lys—
Cys—Lys—Leu—Gly—Ser—Asp—Gly—Glu—Glu—
Asn—Gln—Cys—Val—Thr—Gly—Glu—Gly—Thr—
Pro—Lys—Pro—Gln—Ser—His—Asn—Asp—Gly—
Asp—Phe—Glu—Glu—Ile—Pro—Glu—Glu—Tyr(R)—
Leu—Gln

Ile—Thr—Tyr—Thr—Asp—Cys—Thr—Glu—Ser— (II)
Gly—Gln—Asp—Leu—Cys—Leu—Cys—Glu—Gly—
Ser—Asn—Val—Cys—Gly—Lys—Gly—Asn—Lys—
Cys—Ile—Leu—Gly—Ser—Asn—Gly—Glu—Glu—
Asn—Gln—Cys—Val—Thr—Gly—Glu—Gly—Thr—
Pro—Lys—Pro—Gln—Ser—His—Asn—Asp—Gly—
Asp—Phe—Glu—Glu—Ile—Pro—Glu—Glu—Tyr(R)—
Leu—Gln

Ile—Thr—Tyr—Thr—Asp—Cys—Thr—Glu—Ser— (II')
Gly—Gln—Asp—Leu—Cys—Leu—Cys—Glu—Gly—
Ser—Asp—Val—Cys—Gly—Lys—Gly—Asn—Lys—
Cys—Ile—Leu—Gly—Ser—Asn—Gly—Glu—Glu—
Asn—Gln—Cys—Val—Thr—Gly—Glu—Gly—Thr—
Pro—Lys—Pro—Gln—Ser—His—Asn—Asp—Gly—
Asp—Phe—Glu—Glu—Ile—Pro—Glu—Glu—Tyr(R)—
Leu—Gln

Ile—Thr—Tyr—Thr—Asp—Cys—Thr—Glu—Ser— (IIb)
Gly—Gln—Asn—Leu—Cys—Leu—Cys—Glu—Gly—
Ser—Asn—Val—Cys—Gly—Lys—Gly—Asn—Lys—
Cys—Ile—Leu—Gly—Ser—Asn—Gly—Glu—Glu—
Asn—Gln—Cys—Val—Thr—Gly—Glu—Gly—Thr—
Pro—Lys—Pro—Gln—Ser—His—Asn—Asp—Gly—
Asp—Phe—Glu—Glu—Ile—Pro—Glu—Glu—Tyr(R)—
Leu—Gln

Val—Val—Tyr—Thr—Asp—Cys—Thr—Glu—Ser— (IIIa)
Gly—Gln—Asn—Leu—Cys—Leu—Cys—Glu—Asp—
Ser—Asn—Val—Cys—Gly—Glu—Gly—Asn—Lys—
Cys—Ile—Leu—Gly—Ser—Asn—Gly—Glu—Lys—
Asn—Gln—Cys—Val—Thr—Gly—Glu—Gly—Thr—
Pro—Lys—Pro—Gln—Ser—His—Asn—Asp—Gly—
Asp—Phe—Glu—Glu—Ile—Pro—Glu—Glu—Tyr(R)—
Leu—Gln

Val—Val—Tyr—Thr—Asp—Cys—Thr—Glu—Ser— (IIIa')
Gly—Glu—Asp—Leu—Cys—Leu—Cys—Glu—Gly—
Ser—Asn—Val—Cys—Gly—Glu—Gly—Asn—Lys—
Cys—Ile—Leu—Gly—Ser—Asp—Gly—Glu—Lys—
Asn—Glu—Cys—Val—Thr—Gly—Glu—Gly—Thr—
Pro—Lys—Pro—Gln—Ser—His—Asn—Asp—Gly—
Asp—Phe—Glu—Glu—Ile—Pro—Glu—Glu—Tyr(R)—
Leu—Gln

Val—Val—Tyr—Thr—Asp—Cys—Thr—Glu—Ser— (III)
Gly—Gln—Asn—Leu—Cys—Leu—Cys—Glu—Asp—
Ser—Asn—Val—Cys—Gly—Gln—Gly—Asn—Lys—
Cys—Ile—Leu—Gly—Ser—Asn—Gly—Glu—Lys—

-continued

Asn—Gln—Cys—Val—Thr—Gly—Glu—Gly—Thr—
Pro—Lys—Pro—Gln—Ser—His—Asn—Asp—Gly—
Asp—Phe—Glu—Glu—Ile—Pro—Glu—Glu—Tyr(R)—
Leu—Gln

Val—Val—Tyr—Thr—Asp—Cys—Thr—Glu—Ser— (IIIb)
Gly—Gln—Asn—Leu—Cys—Leu—Cys—Gln—Asp—
Ser—Asn—Val—Cys—Gly—Gln—Gly—Asn—Lys—
Cys—Ile—Leu—Gly—Ser—Asn—Gly—Glu—Lys—
Asn—Gln—Cys—Val—Thr—Gly—Glu—Gly—Thr—
Pro—Lys—Pro—Gln—Ser—His—Asn—Asp—Gly—
Asp—Phe—Glu—Glu—Ile—Pro—Glu—Glu—Tyr(R)—
Leu—Gln

Val—Val—Tyr—Thr—Asp—Cys—Thr—Glu—Ser— (IIIb')
Gly—Gln—Asn—Leu—Cys—Leu—Cys—Gln—Gly—
Ser—Asn—Val—Cys—Gly—Gln—Gly—Asn—Lys—
Cys—Ile—Leu—Gly—Ser—Asn—Gly—Glu—Lys—
Asn—Gln—Cys—Val—Thr—Gly—Glu—Gly—Thr—
Pro—Lys—Pro—Gln—Ser—His—Asn—Asp—Gly—
Asp—Phe—Glu—Glu—Ile—Pro—Glu—Glu—Tyr(R)—
Leu—Gln

The invention in addition relates to a process for the preparation of isohirudins which comprises isolating and purifying isohirudins from leeches with the aid of a combination of extraction methods, precipitation methods and chromatographic methods, if desired hydrolytically splitting off an optionally present phenol ester group R with the formation of the phenolic hydroxyl group and optionally converting the resulting polypeptides into their physiologically tolerable salts.

The isohirudins are preferably first extracted as described by F. Markwardt in Biomed. Biochem. Acta 44 (1985) 1007–1013 or in EP-A 158,986 and EP-A 209,061 and the crude isohirudins are subsequently precipitated. The further isolation and purification is carried out by means of a combination of chromatographic methods as described, for example, by P. Walsmann in Pharmazie 36 (1981) 860–861. Preferably, however, the following combination of chromatography methods is used:

ion exchange chromatography→gel permeation chromatography→affinity chromatography→gel permeation chromatography→ion exchange chromatography→microbore RP-HPLC.

The individual chromatographic methods are generally known per se.

The process according to the invention is distinguished by the combination of the different chromatography methods including the final microbore RP-HPLC, in which columns of 1 mm internal diameter are used. Due to a smaller plate height and the lower diffusion in the column, a higher resolution results in this case than in conventional 4.6 mm columns (R. P. W. Scott, J. Chromatographic Science 23 (1986) 233–237; R. Gill, J. Chromatography 16 (1986) 281).

The microbore RP-HPLC unit used here consists of two Beckman 114M solvent delivery modules which are controlled by a 421 a controller. The buffer line to each pump—made of passivated ⅛ inch V8 steel tube—is connected via a T-piece with a dynamic microgradient mixer which homogenizes the buffer solutions, the resulting pulsations being absorbed by a pulsation damper inserted on-line (Waters part No. 98060) and the buffer solution being introduced into the microbore column via the Reodyne valve of a sample applicator (Gilson Abimed model 231, dilutor model 401). The microbore column packed with Aquapore RP-300 (300 Å pore size) 7 μm spherical silica (Applied Biosystems, Cat. No. 400422 Rp) is in a furnace (Sykam S 4110, temperature 40° C.). Detection is at 205 nm in a UV detector (Sykam S 3300 which is equipped and adjusted for 0.08 AUFS). Recording is carried out by means of a compensating recorder (10 mv FS), and integration using the LAS system (Hewlett Packard) after A/D conversion (HP 18625 A A/D convertor). Linear gradient operation is optimized.

The following mixtures A and B are used as buffers:
A: 90% by weight of water, 10% by weight of acetonitrile (ACCN)+0.1% by volume of trifluoroacetic acid (TFA)
B: 90% by weight of ACCN, 10% by weight of water+0.1% by volume of TFA.

In this connection, 3 different gradients are used for the different separation and purification steps:
a) for the separation of the isohirudins from one another in analytical and preparative operation: 0% B to 40% B (gradient 0.06% B/min)
b) for rechromatography and final purification: 0% B to 35% B (gradient 0.4% B/min)
c) for peptide separation: 0% B to 30% B (gradient 1.7% B/min)

Chromatography is carried out using a flow rate of 80 μl/min and manual fractionation.

It is only possible to carry out further novel peptide separations owing to the use, according to the invention, of microbore RP-HPLC—additionally to the known isolation and purification methods. Unfortunately, however, cases still occur in which for reasons of too large an affinity of the individual components, separation remains incomplete even here. This is, for example, the case with the isohirudins II and II'; IIIa, IIIa'; IIIb and IIIb'. The addition ' thus means that these mutations were found, i.e. were additionally sequenced, during the sequence analysis of the related proteins. Thus, for example, isohirudin II' was found in the analysis of isohirudin II in degradation step 20.

The novel isohirudins described in this application are initially purified by methods known from the literature, including affinity chromatography on thrombin-sepharose columns. The resulting isohirudin mixture is then separated into its components with the aid of microbore RP-HPLC. In the case of serious separation problems, the isolated fractions are rechromatographed under slightly changed conditions. Each novel isohirudin is purified to homogeneity or virtual homogeneity and its sequence is completely elucidated, in some cases not only the amino acid sequence being determined by sequence analysis, but additionally protein chemistry methods, such as specific chemical cleavages, being used in order to prove the novel sequences.

The amino acid analysis is carried out using a Beckmann 6300 amino acid analyzer according to the instructions of the manufacturer. To do this, the proteins (30–50 pmol) were previously dried in a 4×40 mm quartz test tube and subsequently hydrolyzed at 110° C. in the vapor phase using azeotropic HCl/0.8% phenol under a nitrogen atmosphere. For each batch, 500 pmol of insulin standard are additionally analyzed. The results are integrated using the LAS system (Hewlett Packard).

The N-terminal amino acid sequence is determined by automated sequence analysis on the native protein. This is carried out using a 477 A Pulsed Liquid-Phase (TM) protein sequencer from Applied Biosystems, which is linked on-line with a 120 A PTH analyzer with a data analysis system, according to the instructions of the manufacturer.

In some cases, i.e. for the isohirudins I, II, IIb, III and IIIa, a protease-specific peptide cleavage is additionally carried out. To do this, the "disulfide bridges" of the particular proteins are first oxidized using performic acid, by means of which cystine is converted into cysteic acid. This oxidation causes the proteins to lose their spatial configuration and to form a polymer (a knot) of amino acids without a rigidly definable configuration. After the oxidation, the reaction mixture is freeze-dried, the resulting protein is cleaved using trypsin in a suitable buffer, the peptide mixture is separated into the individual components by means of microbore RP-HPLC and isolated in a preparative procedure.

The primary sequence is subsequently determined by amino acid analysis of these peptides. A serine protease, preferably trypsin, which cleaves at a basic amino acid, i.e. at Arg or Lys, is employed for the specific cleavage.

The new isohirudins of the formula A may additionally be prepared analogously to the process described in EP-A 171,024.

The isohirudins according to the invention are specific thrombin inhibitors. The quantitative inhibition of thrombin by the inhibitors according to the invention showed that the thrombin inhibitor/thrombin complex remains virtually undissociated.

The activity and thus the degree of purity of the isohirudins according to the invention can be determined during working up and purification with the aid of the thrombin inhibition test described below. The isohirudins of the general formula (A) thus purified in this case have a thrombin inhibition of 12–16 AT-U/$\mu$g (antithrombin units/$\mu$g).

Thrombin inhibition test for the determination of activity

The test is carried out at room temperature in a total volume of 200 $\mu$l in a 96-well microtiter plate. After preincubating the thrombin (bovine thrombin 50 NIH-U/mg (Merck, Item No. 12374); stock solution: 40 NIH-U/ml in 20 mM MES pH 6, 0.154 mM NaCl, 0.2% PEG 6000, 1% BSA) in a final volume of 100 $\mu$l with 1 to 50 $\mu$l of isohirudin, the reaction is started by addition of substrate. Since the activities tie between 0.03 and 0.15 AT-U in the measuring region of the test, the samples to be determined must be correspondingly diluted using a test buffer.

The required amount of test buffer (50 mM tris/HCl, pH 8; 154 mM NaCl; 0.2% polyethylene glycol 6000) per microtiter plate well is initially introduced. 50 $\mu$l each of 4 NIH-U/ml thrombin solution (see above) and the sample are subsequently added. After an incubation time of 10 minutes, the reaction is then started by the addition of 100 ul of 1 mM Chromozym TH (Boehringer, Item No. 206849; 10 $\mu$m in water/HCl, pH 6; working solution: 1 mM diluted with test buffer). After incubation of the residual thrombin with the chromogen substrate for 5–10 minutes, the nitroaniline reteased is then determined photometrically at 405 nm. A reaction terminator is not required, but an ®ELISA reader (Easy Reader EAR 400 (SLT Labinstruments, Austria) is available for rapidly reading the microtiter plate wells. A hirudin standard is in principle also unnecessary, since an absolute determination of the antithrombin units is possible by means of the use of a defined thrombin activity. Nevertheless, the gradual inactivation of the working solution leads to a systematic error which can be eliminated if the measured values are related to a defined hirudin standard. The test is then independent of the absolute thrombin concentration and permits reproducible determinations.

The following controls are used:

a) Blank

The thrombin solution is replaced by a buffer (photometer zero equatization)

b) Thrombin value

A microtiter plate well is left without inhibitor.

c) Hirudin standard 0.07–0.1 AT-U of a known hirudin standard (Pentapharm hirudin "purified by affinity chromatography", specific activity: 10 AT-U/$\mu$g, concentration: 0.1 AT-U/50 $\mu$l) is added to one microtiter plate well.

In order to determine the concentrations of the samples, a calibration curve for 1 to 20 $\mu$g of isohirudin was determined for the microbore HPLC.

Table 1 which follows compares the concentration values determined on the microbore HPLC with those obtained by the thrombin inhibition test:

TABLE 1

| Isohirudin | Concentration [$\mu$g/ml] | | AT-U/$\mu$g |
| --- | --- | --- | --- |
| | Microbore HPLC | Thrombin inhibition test | |
| Ia | 56 | 59 | 14 |
| I | 56 | 62 | 15 |
| Ib | 34 | 38 | 16 |
| IIa | 68 | 72 | 15 |
| II | 120 | 140 | 16 |
| IIb | 137 | 145 | 16 |
| IIIa | 84 | 87 | 12 |
| III | 397 | 533 | 16 |
| IIIb | 97 | 109 | 14 |

The invention therefore also relates to the use of isohirudins of the formula (A) as blood coagulation inhibitors for use in the prophylaxis and therapy of thromboembolic processes and also to their use as diagnostics and reagents. In addition, the isohirudins according to the invention may also be coupled to a carrier, by means of which derivatives having sustained thrombin-inhibitory action are formed, such as are proposed in German Patent Application P 38 19 079.6.

The invention furthermore relates to pharmaceutical preparations which contain an isohirudin of the formula (A) in a pharmaceutically acceptable excipient.

These preparations may be used, in particular, in the abovementioned indications, when they are administered, for example, parenterally (such as intravenously, intracutaneously, intramuscularly or subcutaneously), orally or topically. The dosage depends primarily on the specific administration form and on the purpose of the therapy or prophylaxis. The size of the individual doses and the administration scheme can best be determined by an individual evaluation of the particular disease case; the methods required for this for the determination of relevant blood factors are familiar to the expert. In the normal case, with one injection the therapeutically effective amount of the isohirudins according to the invention is in the dose range from about 0.005 to about 0.1 mg/kg of body weight. The range from about 0.01 to about 0.05 mg/kg of body weight is preferred. Administration is carried out by intravenous, intramuscular or subcutaneous injection. Accordingly, pharmaceutical preparations for parenteral administration in single-dose form contain about 0.4 to about 7.5 mg of the isohirudin according to the invention depending on the type of administration. In addition to the active compound, these pharmaceutical preparations customarily contain a buffer, for example a phosphate buffer, which should keep the pH between about 3.5 and 7, and in addition sodium chloride, mannitol or sorbitol for adjusting the isotonicity. They may be present in freeze-dried or dissolved form, it being possible for solutions to advantageously contain an antibacterially active preservative, for example 0.2 to 0.3% of methyl or ethyl 4-hydroxybenzoate.

A preparation for topical application may be present as an aqueous solution, lotion or get, an oily solution or suspension, or a fat-containing or, in particular, emulsion ointment. A preparation in the form of an aqueous solution is obtained, for example, by dissolving the active compounds according to the invention or a therapeutically utilizable salt thereof in an aqueous buffer solution of pH 4 to 6.5 and, if desired, adding a further active compound, for example an antiinflammatory, and/or a polymeric adhesive, for example polyvinylpyrrolidone, and/or a preservative. The concentration of the active compound is about 0.08 to about 1.5 mg, preferably 0.25 to 1.0 mg, in about 10 ml of a solution or 10 g of a gel.

An oily administration form for topical application is obtained, for example, by suspending the active compounds according to the invention or a therapeutically utilizable salt thereof in an oil, if desired using swelling agents, such as aluminum stearate, and/or surface-active agents (surfactants), the HLB value ("hydrophilic-lipophilic balance") of which is under 10, such as fatty acid monoesters of polyhydric alcohols, for example glycerol monostearate, sorbitan monolaurate, sorbitan monostearate or sorbitan monooleate. A fat-containing ointment is obtained, for example, by suspending the active compounds according to the invention or their salts in a spreadable fatty foundation, if desired using a surfactant of HLB value under 10. An emulsion ointment is obtained by triturating an aqueous solution of the active compounds according to the invention or their salts in a soft, spreadable fatty foundation with the addition of a surfactant, the HLB value of which is under 10. All these topical application forms may also contain preservatives. The concentration of the active compound is about 0.08 to about 1.5 mg, preferably 0.25 to 1.0 mg, in about 10 g of the foundation.

In addition to the pharmaceutical compositions described above and their analogues, which are intended for direct medicinal use on the human or mammalian body, the present invention also relates to pharmaceutical compositions and preparations for medicinal use outside the living human or mammalian body. Such compositions and preparations are used primarily as coagulation-inhibiting additives for blood which is subjected outside the body to a circulation or treatment (for example dialysis in artificial kidneys), preservation or modification (for example hemoseparation). In their composition, preparations of this type, such as stock solutions or else preparations in single-dose form, are similar to the injection preparations described above; expediently, however, the amount or concentration of active compound is related to the volume of the blood to be treated or, more exactly, to its thrombin content. In this connection, it is to be observed that the active compounds according to the invention (in free form)
(a) deactivate an approximately 5-fold amount by weight of thrombin completely;
(b) are physiologically harmless even in relatively large amounts; and
(c) are excreted very rapidly from the circulating blood even in high concentrations, so that no risk of overdosage exists, even, for example, with transfusions. Depending on the specific purpose, the suitable dose is about 0.01 to about 1.0 mg of active compound/l of blood, it still being possible for the upper limit to be far exceeded without risk.

The present invention also relates to the bioanalytical application of the compounds according to the invention and their salts for the determination of thrombin, and also preparations serving this purpose and containing the active compounds according to the invention, for example solid mixtures and above all solutions, in particular aqueous solutions; these may also expediently contain inert auxiliaries, for example those mentioned above in connection with injection preparations which, for example, have a stabilizing and/or preserving function, in addition to an exact amount or concentration of the active compounds according to the invention, also in the form of a salt. These preparations are used in bioanalyses in analogous, known ways like the hirudin preparations, for example for the determination of thrombin.

The compounds according to the invention can moreover be used for blood preservation. For this purpose, the compounds according to the invention are advantageously added to blood preserves in an amount of 0.1–2% by weight.

BRIEF DESCRIPTION OF THE DRAWING

The Drawing depicts HPLC resolution of an active hirudin fraction.

The examples which follow serve to illustrate the invention. The one-letter code is used as an abbreviation for amino acids here in contrast to the foregoing description and the claims.

| Three- and one-letter code for amino acids | | | |
|---|---|---|---|
| Amino acid | Abbreviation | Amino acid | Abbreviation |
| Alanine | Ala (A) | Proline | Pro (P) |
| Arginine | Arg (R) | Serine | Ser (S) |
| Cysteine | Cys (C) | Threonine | Thr (T) |
| Glycine | Gly (G) | Tryptophan | Trp (W) |
| Histidine | His (H) | Tyrosine | Tyr (Y) |
| Isoleucine | Ile (I) | Valine | Val (V) |
| Leucine | Leu (L) | Asparaginic acid | Asp (D) |
| Lysine | Lys (K) | Asparagine | Asn (N) |
| Methionine | Met (M) | Glutamic acid | Glu (E) |
| Phenylalanine | Phe (F) | Glutamine | Gln (Q) |

EXAMPLE 1

Isolation of isohirudins Ia, I, Ib, IIa, II, IIb, IIIa, III, IIIb, oxidation, tryptic cleavage, sequence analysis and amino acid analysis a) Isolation The isolation of the new isohirudins initially followed the methods known from the Literature (P. Walsmann, Thrombosis Research 40 (1985) 563–569). The most important steps should only be mentioned here. After the extraction of the front part of the leeches with 40% acetone and precipitation of ballast materials with glacial acetic acid, the enriched hirudin extract was precipitated using acetone. The precipitate was purified via ion exchange (for example ®DEAE Sephacel) in tris/HCl buffer (pH 7.4) with the aid of a saline gradient. The fractions active in the antithrombin test were combined and freeze-dried. The buffer components were then separated in portions via ®Sephadex G 25 in water, the active fractions were applied to a thrombin-sepharose column in 0.1M tris/HCl buffer (PH 8.0) and, after washing with the same buffer, eluted with 0.1M sodium acetate 0.5M sodium chloride (pH 5.0). Part of the hirudin was also eluted in the course of this. The pure hirudin fractions were then eluted using 0.1M tris/HCl/1.5M benzamidine (pH 8.0). By coupling the thrombinsepharose to a ®Sephadex G 25 column, the elution of the hirudin was subsequently performed together with separation of the thrombin inhibitor benzamidine at reduced flow. After freeze-drying, the active fractions were purified by ion exchange chromatography over SE-®Sephadex in 0.01M ammonium acetate buffer (pH 3.8) and elution with a gradient of sodium chloride. Three active fractions were isolated. Fraction II was desalted over ®Sephadex and freeze-dried. The specific activity was 12 AT-U/ug.

The non-homogeneous fraction II was employed for microbore RP-HPLC. Using very shallow gradients (0.06% of B per minute), the mixture was resolved into three principal peaks having very different retention times (RT) (peak I: RT about 89 minutes; peak II: RT about 113 minutes; peak III: RT about 134 minutes; see Drawing). These principal peaks are accompanied by smaller satellite peaks (a and b). Peak IIIa designates, for example, the satellite peak having an RT of about 130 minutes which is eluted immediately before the principal peak III. Correspondingly, the satellite peak IIIb (RT about 139 minutes) is used which is eluted after the principal peak III.

By carefully increasing the amount injected and collecting the fractions (peaks), the microbore RP-HPLC unit was used for preparative isolation of the different isohirudin variants. Up to 50 μg were injected and the various fractions (peaks) were collected without noting losses in the resolution of the peaks. In order to isolate a sufficient amount, this procedure was repeated several times and the identical fractions were combined and freeze-dried. The different rechromatographed peaks were then finally purified by "narrower" fractionations. In this way, the isohirudins Ia, I, Ib, IIa, II, IIb, IIIa, III and IIIb were separated.

The pure substances were oxidized according to need and cleaved with trypsin.

b) Oxidative cleavage of the disulfides

100 μl of performic acid solution (prepared from 50 μl of hydrogen peroxide and 950 μl of formic acid; left to stand at room temperature for 2.5 hours) were added to the isohirudins. After 30 minutes, the mixture was diluted with 200 μl of water and then freeze-dried.

c) Trypsin cleavage

The oxidized isohirudins were taken up in 50 μl of NMM buffer (0.2M N-methyloorpholine adjusted to pH 8 with glacial acetic acid). A solution of trypsin in NMM buffer in the ratio substrate:enzyme=1:100 was added to this. After 30 minutes at room temperature, the reaction was stopped by addition of 100 μl of glacial acetic acid. This resulting mixture was then used further for microbore RP-HPLC.

d) Sequence analysis

The isolated and purified isohirudins were sequenced using a 477A Pulsed liquid Phase (TM) protein sequencer (Applied Biosystems) which is coupled on-line with a 120A PTH analyzer having a data analysis system. The sequencing was carried out according to the instructions of the manufacturer. The results are shown in Tables 3 to 15.

e) Amino acid analysis

The amino acid composition of the individual isohirudins was determined using a Beckman 6300 amino acid analyzer. In this connection, the analysis was carried out according to the instructions of the manufacturer. The reagents and the separating column were likewise bought from the manufacturer. Subsequent integration was carried out using the LAS system (Hewlett Packard). The proteins (about 30–50 pmol) were dried in a 4×40 mm quartz test tube and hydrolyzed at 110° C. in the vapor phase by azeotropic HCl/0.8% phenol under a nitrogen atmosphere. 500 pmol of insulin standard were additionally analyzed for each batch.

Table 2 which follows shows the results obtained.

TABLE 2

| | Amino acid analysis | | | | | | | | | | | | | | | | |
|---|---|---|---|---|---|---|---|---|---|---|---|---|---|---|---|---|---|
| | Isohirudins | | | | | | | | | | | | | | | | |
| | Ia | | I | | IIa | | II | | IIb | | IIIa | | III | | IIIb | |
| Isohirudine | a | b | a | b | a | b | a | b | a | b | a | b | a | b | a | b |
| Asx | 9.6 | 9 | 9.8 | 10 | 9.9 | 10 | 9.1 | 9 | 9.2 | 9 | 10 | 10 | 10 | 10 | 9.5 | 10 |
| Thr | 3.8 | 4 | 3.7 | 4 | 4.7 | 5 | 4.5 | 5 | 4.6 | 5 | 3.9 | 4 | 3.8 | 4 | 3.7 | 4 |
| Ser | 3.4 | 4 | 3.4 | 4 | 3.6 | 4 | 5.6 | 4 | 3.7 | 4 | 3.7 | 4 | 4 | 4 | 3.2 | 4 |
| Glx | 12.2 | 12 | 13.3 | 12 | 13.2 | 13 | 13.9 | 13 | 13.2 | 13 | 13.6 | 13 | 13.7 | 13 | 13.1 | 13 |
| Pro | 2.3 | 3 | 2 | 3 | 2.2 | 3 | 2.1 | 3 | 2.1 | 3 | 2.1 | 3 | 2.2 | 3 | 2.4 | 3 |
| Gly | 9.3 | 9 | 9 | 9 | 9.6 | 9 | 10.1 | 9 | 9.1 | 9 | 9.4 | 9 | 9.4 | 9 | 9.1 | 9 |
| Cys/2 | 4 | 6 | 4.5 | 6 | 3.9 | 6 | 3.6 | 6 | 4.5 | 6 | 4.8 | 6 | 3.9 | 6 | 4.1 | 6 |
| Val | 2.9 | 4 | 3.0 | 4 | 1.9 | 2 | 1.9 | 2 | 1.8 | 2 | 2.9 | 4 | 2.5 | 4 | 2.8 | 4 |
| Ile | 1.8 | 2 | 1.8 | 2 | 1.7 | 2 | 2.3 | 2 | 1.8 | 2 | 1.9 | 2 | 1.7 | 2 | 1.9 | 2 |
| Leu | 3.7 | 4 | 4.0 | 4 | 3.8 | 4 | 3.4 | 4 | 4 | 4 | 4.2 | 4 | 3.9 | 4 | 4 | 4 |
| Tyr | 1.9 | 2 | 1.9 | 2 | 1.8 | 2 | 0.6 | 2 | 1.9 | 2 | 1.7 | 2 | 1.2 | 2 | 1.7 | 2 |
| Phe | 0.9 | 1 | 0.9 | 1 | 1 | 1 | 0.9 | 1 | 0.9 | 1 | 1 | 1 | 1 | 1 | 1 | 1 |
| His | 1 | 1 | 0.9 | 1 | 0.9 | 1 | 1.3 | 1 | 0.1 | 1 | 0.9 | 1 | 1 | 1 | 0.9 | 1 |
| Lys | 2.8 | 4 | 2.9 | 3 | 3.1 | 3 | 2.5 | 3 | 2.8 | 3 | 3 | 3 | 2.9 | 3 | 2.7 | 3 | a: found
b: calculated

In Examples 2 to 9 which follow the analysis was carried out analogously to the methods indicated in Example 1. The corresponding data concerning the specific activity and the amino acid analyses are indicated in Tables 1 and 2.

EXAMPLE 2

Isohirudin I

Isohirudin I was isolated from the peak I (RT about 89 minutes) and purified by rechromatography. N-terminal sequence analysis made it possible to determine the structure up to 30 amino acids (Table 3). After oxidation and tryptic cleavage, the fragments T2 and T3 (C-terminal peptide) were isolated and the sequences elucidated. The results are shown in Table 4.

TABLE 3

Quantitative sequence analysis of isohirudin I

| | 1 | | | | 5 | | | | | 10 | | |
|---|---|---|---|---|---|---|---|---|---|---|---|---|
| Amino acid | V | V | Y | T | D | C | T | E | S | G | Q | N |
| pmol | 107 | 90 | 76 | 48 | 30 | nd | 21 | 29 | 13 | 30 | 19 | 20 |
| | | | 15 | | | | | | | | | |
| Amino acid | L | C | L | C | E | G | S | N | V | C | G | N* |
| pmol | 18 | nd | 6 | nd | 11 | 16 | 12 | 17 | 15 | nd | 12 | 13 |
| | 25 | | | | | 30 | | | | | 35 | |
| Amino acid | G | N | K | C | I | L | G | S | D | G | E | K |
| pmol | 11 | 8 | 6 | nd | 5 | 5 | | | | | | |
| | | | | 40 | | | 45 | | | | | |
| Amino acid | N | Q | C | V | T | G | E | G | T | P | K | P |
| pmol | | | | | | | | | | | | |
| | 50 | | | | | 55 | | | | | 60 | |
| Amino acid | Q | S | H | N | D | G | D | F | E | E | I | P |
| pmol | | | | | 65 | | | | | | | |
| Amino acid | E | E | Y | L | Q | | | | | | | |

TABLE 3-continued

Quantitative sequence analysis of isohirudin I

```
pmol  V V Y T D C T E S G Q N L C L C E G S N         (1)
      V C G Q G N K C I L G S D G E K N Q C V
      T G E G T P K P Q S H N D G D F E E I P
      E E Y* L Q
```

*amino acid exchange in comparison to (1)
nd: not determinable
Y* Sulfatotyrosine

TABLE 4

Quantitative sequence analysis of the tryptic cleavage products of isohirudin I

| Peptide T2 | | | | | | | | | |
|---|---|---|---|---|---|---|---|---|---|
| | 28 | | 30 | | | | 35 | | |
| Amino acid T2 | C | I | L | G | S | D | G | E | K |
| pmol | nd | 204 | 156 | 128 | 40 | 63 | 68 | 23 | 8 |
| Peptide T3 | | | | | | | | | | |
| | 37 | | | 40 | | | | 45 | | |
| Amino acid T3 | N | Q | C | V | T | G | E | G | T | P | K | P |
| pmol | 159 | 178 | nd | 105 | 89 | 122 | 89 | 86 | 63 | 57 | 58 | 25 |
| | | 50 | | | | | 55 | | | | 60 | |
| Amino acid T3 | Q | S | H | N | D | G | D | F | E | E | I | P |
| pmol | 36 | 12 | 6 | 12 | 9 | 10 | 11 | 7 | 7 | 3 | 4 | 5 |
| | | | | | 65 | | | | | | | |
| Amino acid T3 | E | E | Y | L | Q | | | | | | | |
| pmol | 4 | 4 | 1 | 1 | 3 | | | | | | | | nd: not determinable

EXAMPLE 3

Isohirudin Ia

Isohirudin Ia was isolated from the protein mixture which was obtained before the peak I (RT about 85 minutes) analogously to Example I. The product was purified by rechromatography. Subsequent N-terminal sequence analysis made it possible to determine the total structure (Table 5).

TABLE 5

Quantitative sequence analysis of isohirudin Ia

| | 1 | | | | 5 | | | | | 10 | | |
|---|---|---|---|---|---|---|---|---|---|---|---|---|
| Amino acid | V | V | Y | T | D | C | T | E | S | G | Q | N |
| pmol | 336 | 334 | 297 | 614 | 161 | nd | 339 | 114 | 241 | 185 | 196 | 181 |
| | | | 15 | | | | | 20 | | | | |
| Amino acid | L | C | L | C | E | G | S | N | V | C | G | K* |
| pmol | 188 | nd | 173 | nd | 123 | 156 | 130 | 149 | 146 | nd | 132 | 118 |
| | 25 | | | | | 30 | | | | | 35 | |
| Amino acid | G | N | K | C | I | L | G | S | D | G | E | K |
| pmol | 122 | 118 | 78 | nd | 71 | 84 | 71 | 53 | 69 | 76 | 60 | 69 |
| | | | | 40 | | | | 45 | | | | |
| Amino acid | N | Q | C | V | T | G | E | G | T | P | K | P |
| pmol | 60 | 61 | nd | 46 | 39 | 43 | 37 | 39 | 24 | 16 | 28 | 19 |
| | | 50 | | | | | 55 | | | | 60 | |
| Amino acid | Q | S | H | N | D | G | D | F | E | E | I | P |
| pmol | 17 | 11 | 6 | 16 | 12 | 9 | 11 | 13 | 6 | 5 | 5 | 3 |
| | | | | | 65 | | | | | | | |
| Amino acid | E | E | Y | L | Q | | | | | | | |
| pmol | 4 | 4 | 3 | 3 | 2 | | | | | | | |

*amino acid exchange in comparison to (1)
nd: not determinable

EXAMPLE 4

Isohirudin IIa

Isohirudin IIa was isolated from the peak IIa (RT about 107 minutes) and purified by rechtomatography.

The structure was elucidated by N-terminal sequence analysis (Table 6).

minal peptide (28-65) was isolated by oxidation and tryptic cleavage and the sequence was determined

TABLE 6

Quantitative sequence analysis of isohirudin IIa

| Amino acid | 1<br>I* | T* | Y | T | 5<br>D | C | T | E | S | 10<br>G | Q | N |
|---|---|---|---|---|---|---|---|---|---|---|---|---|
| pmol | 423 | 372 | 377 | 310 | 368 | nd | 392 | 274 | 295 | 261 | 287 | 271 |
| Amino acid | L | C | 15<br>L | C | E | G | 20<br>S | N | V | C | G | N* |
| pmol | 258 | nd | 241 | nd | 230 | 228 | 227 | 226 | 218 | nd | 223 | 210 |
| Amino acid | 25<br>G | N | K | C | 30<br>K* | L | G | S | D | 35<br>G | E | E* |
| pmol | 191 | 149 | 200 | nd | 171 | 182 | 169 | 176 | 162 | 145 | 135 | 125 |
| Amino acid | N | Q | C | 40<br>V | T | G | E | G | 45<br>T | P | K | P |
| pmol | 115 | 126 | nd | 107 | 105 | 96 | 93 | 92 | 79 | 72 | 71 | 62 |
| Amino acid | Q | 50<br>S | H | N | D | G | 55<br>D | F | E | E | I | 60<br>P |
| pmol | 60 | 49 | 55 | 52 | 50 | 41 | 43 | 47 | 30 | 31 | 30 | 16 |
| Amino acid | E | E | Y | L | 65<br>Q | | | | | | | |
| pmol | 15 | 15 | 17 | 12 | 12 | | | | | | | |

*amino acid exchange in comparison to (1)
nd: not determinable

EXAMPLE 5

Isohirudins II and II'

Isohirudins II and II' were isolated as a mixture from fraction II (peak II; RT about 113 minutes) and purified by rechromatography analogously to Example 1. The sequence of the isohirudins up to amino acid 35 was elucidated by N-terminal sequence analysis. The C-ter- (Table 8). The total sequence analysis of the isohirudins II and II' is indicated in Table 7. Isohirudin II' was in this case characterized during the sequence analysis of the isohirudin mixture II and II', as already explained previously. Isohirudin II' differs from isohirudin II by the exchange of asparagine for asparaginic acid in position 20.

TABLE 7

Quantitative sequence analysis of isohirudins II and II'

| | 1 | | | | 5 | | | | | 10 | | |
|---|---|---|---|---|---|---|---|---|---|---|---|---|
| Amino acid II | I* | T* | Y | T | D | C | T | E | S | G | Q | D* |
| pmol | 311 | 268 | 278 | 267 | 242 | nd | 169 | 175 | 165 | 144 | 165 | 163 |
| | | | 15 | | | | | 20 | | | | |
| Amino acid II | L | C | L | C | E | G | S | N | V | C | G | K* |
| pmol | 150 | nd | 132 | nd | 124 | 109 | 116 | 124 | 110 | nd | 111 | 110 |
| Amino acid II' | | | | | | | | D** | | | | |
| pmol | | | | | | | | 4 | | | | |
| | 25 | | | | 30 | | | | | 35 | | |
| Amino acid II | G | N | K | C | I | L | G | S | N* | G | E | E* |
| pmol | 98 | 89 | 74 | nd | 66 | 55 | 43 | 70 | 49 | 51 | 45 | 28 |
| | | | | 40 | | | | | 45 | | | |
| Amino acid II | N | Q | C | V | T | G | E | G | T | P | K | P |
| pmol | 20 | 22 | nd | 17 | 12 | 13 | 10 | 3 | 15 | | | |
| | | 50 | | | | | 55 | | | | | 60 |
| Amino acid II | Q | S | H | N | D | G | D | F | E | E | I | P |
| pmol | | | | | | | | | | | | |
| | | | | | 65 | | | | | | | |
| Amino acid II | E | E | Y | L | Q | | | | | | | |
| pmol | | | | | | | | | | | | |

*amino acid exchange in comparison to (1)
**amino acid exchange in comparison to II
nd: not determinable

TABLE 8

Quantitative sequence analysis of the tryptic cleavage products of isohirudins II and II'

| | 28 | | 30 | | | | | 35 | | | | |
|---|---|---|---|---|---|---|---|---|---|---|---|---|
| Amino acid | C | I | L | G | S | N* | G | E | E* | N | Q | C |
| pmol | nd | 266 | 242 | 250 | 223 | 217 | 184 | 178 | 178 | 169 | 145 | nd |
| | 40 | | | | | 45 | | | | 50 | | |
| Amino acid | V | T | G | E | G | T | P | K | P | Q | S | H |
| pmol | 144 | 125 | 138 | 126 | 125 | 137 | 118 | 112 | 102 | 125 | 91 | 113 |
| | | | | 55 | | | | | 60 | | | |

TABLE 8-continued

Quantitative sequence analysis of the tryptic cleavage products of isohirudins II and II'

| Amino acid | N | D | G | D | F | E | E | I | P | E | E | Y |
|---|---|---|---|---|---|---|---|---|---|---|---|---|
| pmol | 117 | 100 | 106 | 97 | 99 | 83 | 79 | 80 | 68 | 59 | 63 | 41 |
| | | 65 | | | | | | | | | | |
| Amino acid | L | Q | | | | | | | | | | |
| pmol | 38 | 16 | | | | | | | | | | |

*amino acid exchange in comparison to (1)
nd: not determinable

EXAMPLE 6

Isohirudin IIb

Isohirudin IIb was isolated from the protein mixture after peak II (RT about 115 minutes) and purified by rechromatography analogously to Example 1. The total sequence shown in Table 9 was determined by N-terminal sequence analysis. A trypsin cleavage was additionally carried out which led to the isolation of the peptide 28–65 (Table 10). The corresponding sequence was determined.

EXAMPLE 7

Isohirudins IIIa and IIIa'

Isohirudins IIIa and IIIa' were isolated from the peak having an RT of about 126 minutes and purified by rechromatography. N-terminal sequence analysis made it possible to determine the structure up to the carboxyl terminus (Table 11). Isohirudin IIIa' was characterized during the sequence analysis as already explained previously. Isohirudin IIIa' differs from isohirudin IIIa by exchange of glutamic acid for glutamine in position 11,

TABLE 9

Quantitative sequence analysis of isohirudin IIb

| | 1 | | | | 5 | | | | | 10 | | |
|---|---|---|---|---|---|---|---|---|---|---|---|---|
| Amino acid | I* | T* | Y | T | D | C | T | E | S | G | Q | N |
| pmol | 378 | 502 | 244 | 465 | 445 | nd | 377 | 400 | 396 | 303 | 291 | 281 |
| | | | 15 | | | | | 20 | | | | |
| Amino acid | L | C | L | C | E | G | S | N | V | C | G | K* |
| pmol | 279 | nd | 269 | nd | 240 | 248 | 248 | 235 | 235 | nd | 259 | 231 |
| | 25 | | | | | 30 | | | | | 35 | |
| Amino acid | G | N | K | C | I | L | G | S | N* | G | E | E* |
| pmol | 215 | 230 | 219 | nd | 221 | 222 | 217 | 210 | 206 | 200 | 195 | 195 |
| | | | | 40 | | | | | 45 | | | |
| Amino acid | N | Q | C | V | T | G | E | G | T | P | K | P |
| pmol | 185 | 174 | nd | 163 | 156 | 145 | 132 | 140 | 129 | 112 | 105 | 91 |
| | | 50 | | | | | 55 | | | | | 60 |
| Amino acid | Q | S | H | N | D | G | D | F | E | E | I | P |
| pmol | 86 | 80 | 72 | 71 | 65 | 54 | 51 | 42 | 46 | 33 | 24 | 26 |
| | | | | | 65 | | | | | | | |
| Amino acid | E | E | Y | L | Q | | | | | | | |
| pmol | 18 | 18 | 15 | 12 | 10 | | | | | | | |

*amino acid exchange in comparison to (1)

TABLE 10

Quantitative sequence analysis of the tryptic peptide of isohirudin IIb

| | 28 | | 30 | | | | 35 | | | | | |
|---|---|---|---|---|---|---|---|---|---|---|---|---|
| Amino acid | C | I | L | G | S | N* | G | E | E* | N | Q | C |
| pmol | 300 | 379 | 381 | 368 | 347 | 337 | 332 | 316 | 305 | 293 | 271 | nd |
| | 40 | | | | | 45 | | | | | 50 | |
| Amino acid | V | T | G | E | G | T | P | K | P | Q | S | H |
| pmol | 255 | 249 | 234 | 228 | 212 | 205 | 197 | 167 | 154 | 143 | 133 | 127 |
| | | | | | 55 | | | | | 60 | | |
| Amino acid | N | D | G | D | F | E | E | I | P | E | E | Y |
| pmol | 112 | 102 | 115 | 100 | 91 | 81 | 78 | 64 | 54 | 32 | 22 | 18 |
| | | 65 | | | | | | | | | | |
| Amino acid | L | Q | | | | | | | | | | |
| pmol | 14 | 12 | | | | | | | | | | |

*amino acid exchange in comparison to (1)
nd: not determinable asparaginic acid for asparagine in position 12, glycine for asparaginic acid in position 18 and asparaginic acid for asparagine in position 33.

TABLE 11

Quantitative sequence analysis of the isohirudins IIIa and IIIa'

| | 1 | | | | 5 | | | | | 10 | | |
|---|---|---|---|---|---|---|---|---|---|---|---|---|
| Amino acid IIIa | V | V | Y | T | D | C | T | E | S | G | Q | N |
| pmol | 660 | 675 | 666 | 477 | 407 | nd | 321 | 458 | 238 | 390 | 269 | 282 |

TABLE 11-continued

Quantitative sequence analysis of the isohirudins IIIa and IIIa'

| | | | | | | | | | | | | E** | D** |
|---|---|---|---|---|---|---|---|---|---|---|---|---|---|
| Amino acid IIIa' | | | | | | | | | | | | | |
| pmol | | | | | | | | | | | | 46 | 33 |
| | | | 15 | | | | 20 | | | | | | |
| Amino acid IIIa | L | C | L | C | E | D* | S | N | V | C | G | E* | |
| pmol | 318 | nd | 284 | nd | 269 | 247 | 239 | 227 | 218 | nd | 204 | 185 | |
| Amino acid IIIa' | | | | | | G** | | | | | | E* | |
| pmol | | | | | | | | | | | | | |
| | 25 | | | | | 30 | | | | 35 | | | |
| Amino acid IIIa | G | N | K | C | I | L | G | S | N* | G | E | K | |
| pmol | 178 | 169 | 161 | nb | 150 | 157 | 154 | 137 | 131 | 128 | 125 | 120 | |
| Amino acid IIIa' | | | | | | | | | D** | | | | |
| pmol | | | | | | | | | | | | | |
| | | | | 40 | | | | | 45 | | | | |
| Amino acid IIIa | N | E* | C | V | T | G | E | G | T | P | K | P | |
| pmol | 88 | 84 | nd | 73 | 62 | 69 | 63 | 59 | 51 | 45 | 53 | 38 | |
| | | 50 | | | | 55 | | | | | 60 | | |
| Amino acid IIIa | Q | S | H | N | D | G | D | F | E | E | I | P | |
| pmol | 32 | 33 | 21 | 22 | 18 | 15 | 13 | 10 | 10 | 11 | 8 | 6 | |
| | | | | | 65 | | | | | | | | |
| Amino acid IIIa | E | E | Y | L | Q | | | | | | | | |
| pmol | 6 | 5 | 5 | 4 | 3 | | | | | | | | |

*amino acid exchange in comparison to (1)
**amino acid exchange in comparison to IIIa
nd: not determinable

EXAMPLE 8

Isohirudin III

Isohirudin III was isolated from the peak having an RT of about 139 minutes and purified by rechromatography.

N-terminal sequence analysis in combination with sequence analysis of the tryptic cleavage products (peptide 28-65) made possible the structure determination of the complete protein (Tables 12 and 13).

Compared to all isohirudins described here, isohirudin III was isolated in a relatively large amount so that the protein-chemical structure proof of the mutation asparaginic acid to asparagine was additionally carried out with this substance.

Bornstein (Methods in Enzymol. 47 (1977) 132-145) described a selective cleavage of Asn-Gly-peptide bonds using the nucleophilic agent hydroxylamine. Accordingly, a buffer was initially prepared which contained 6M guanidinium hydrochloride and 2M hydroxylamine. To this end, 23 g of guanidinium hydrochloride and 5.5 g of hydroxylamine were combined in an icebath with some water and dissolved with vigorous stirring using 4.5M LiOH, the pH not exceeding 6.5. The pH was then adjusted to 9 and the solution was made up to 50 ml with water.

Isohirudin III (about 2 nmol) was lyophilized, taken up using 200 μl of the buffer prepared and then incubated for 4 hours at 45° C. in a waterbath. 200 μl of glacial acetic acid (pH 3) was added to complete the reaction and the sample was frozen. The sample was then concentrated to 200 μl and desalted on a reversed-phase column (4.6 mm×250 mm), packed with C-18 modified silica gel. The gradient in this case ran from 0% to 100% of B in 30 minutes with a flow of 1 ml/min (buffer A: 100% of water, 0.1% of TFA; buffer 8: 90% of ACCN, 10% of water, 0.1% of TFA). The resulting main fraction was then rechromatographed with the aid of microbore HPLC. A fraction F1 was isolated which contained two N terminals after characterization by sequence analysis (Table 14), namely Val Val Tyr and Gly Glu Lys.

Isohirudin III was held together even after hydroxyl cleavage by the cysteine linkage (Cys6-Cys14, Cys16-Cys28, Cys22-Cys39).

TABLE 12

Quantitative sequence analysis of isohirudin III

| | 1 | | | | 5 | | | | | 10 | | |
|---|---|---|---|---|---|---|---|---|---|---|---|---|
| Amino acid III | V | V | Y | T | D | C | T | E | S | G | Q | N |
| pmol | 615 | 569 | 468 | 377 | 265 | nd | 178 | 250 | 108 | 214 | 147 | 195 |
| | | | | 15 | | | | 20 | | | | |
| Amino acid III | L | C | L | C | E | D* | S | N | V | C | G | Q |
| pmol | 158 | nd | 83 | nd | 102 | 88 | 72 | 64 | 54 | nd | 50 | 48 |
| | 25 | | | | | 30 | | | | 35 | | |
| Amino acid III | G | N | K | C | I | L | G | S | N* | G | E | K |
| pmol | 32 | 37 | 29 | nd | 28 | 30 | 23 | 19 | 14 | 17 | 16 | 12 |
| | | | | 40 | | | | | 45 | | | |
| Amino acid III | N | Q | C | V | T | G | E | G | T | P | K | P |

TABLE 12-continued

Quantitative sequence analysis of isohirudin III

| III pmol | 10 | 9 (50) | nd | 5 | 3 | 5 | 6 (55) | 4 | 2 | 1 | 1 | 3 (60) |
|---|---|---|---|---|---|---|---|---|---|---|---|---|
| Amino acid III | Q | S | H | N | D | G | D | F | E | E | I | P |
| pmol | 1 | 0.5 | 1 | 1 | 5 (65) | 1.5 | 0.3 | 0.8 | 2 | 2 | 1.5 | 1 |
| Amino acid III | E | E | Y | L | Q | | | | | | | |
| pmol | 1 | 0.4 | 0.6 | 0.8 | 0.6 | | | | | | | |

*amino acid exchange in comparison to (1)
nd: not determinable

TABLE 13

Quantitative sequence analysis of the tryptic peptides of isohirudin III

| | 28 | | 30 | | | | | 35 | | | | |
|---|---|---|---|---|---|---|---|---|---|---|---|---|
| Amino acid | C | I | L | G | S | N* | G | E | K | N | Q | C |
| pmol | nd (40) | 301 | 295 | 286 | 234 | 273 (45) | 246 | 242 | 219 | 194 | 139 (50) | nd |
| Amino acid | V | T | G | E | G | T | P | K | P | Q | S | H |
| pmol | 151 | 136 | 141 | 149 (55) | 117 | 99 | 82 | 87 | 71 (60) | 68 | 64 | 58 |
| Amino acid | N | D | G | D | F | E | E | I | P | E | E | Y |
| pmol | 51 | 41 (65) | 36 | 30 | 25 | 24 | 27 | 21 | 12 | 16 | 15 | 12 |
| Amino acid | L | Q | | | | | | | | | | |
| pmol | 0.7 | 2 | | | | | | | | | | |

*amino acid exchange in comparison to (1)
nd: not determinable

TABLE 14

Quantitative sequence analysis of the fraction F1 from the hydroxylamine cleavage

| Degradation step | 1 | 2 | 3 | 4 |
|---|---|---|---|---|
| Sequence position | 1 | 2 | 3 | 4 |
| Amino acid: N-terminal | V | V | Y | T |
| pmol | 17 | 17 | 24 | 22 |
| Sequence position | 34 | 35 | 36 | 37 |
| Amino acid: cleavage site | G | E | K | N |
| pmol | 41 | 50 | 37 | 34 |

The finding of two N terminals for F1 is clear proof for hydroxylamine cleavage in the sequence of isohirudin III on the peptide bond N-G

EXAMPLE 9

Isohirudins IIIb and IIIb'

Isohirudins IIIb and IIIb' were isolated analogously to Example 1 from the peak having an RT of about 134 minutes and purified by rechromatography. The structure of isohirudin IIIb to the carboxyl end was characterized by N-terminal sequence analysis (Table 15). The structure of isohirudin IIIb', which was likewise determined in the sequence analysis, is also shown in Table 15.

TABLE 15

Quantitative sequence analysis of isohirudins IIIb and IIIb'

| | 1 | | | | 5 | | | | | 10 | |
|---|---|---|---|---|---|---|---|---|---|---|---|
| Amino acid IIIb | V | V | Y | T | D | C | T | E | S | G | Q | N |
| pmol | 530 | 511 | 499 (15) | 433 | 460 | nd | 395 | 332 (20) | 339 | 326 | 321 | 278 |
| Amino acid IIIb | L | C | L | C | Q | D* | S | N | V | C | G | Q |
| pmol | 264 | nd | 258 | nd | 246 | 240 | 221 | 224 | 195 | nd | 185 | 175 |
| Amino acid IIIb' pmol | | | | | | G** (25) (30) | | | | | (35) | |
| Amino acid IIIb | G | N | K | C | I | L | G | S | N* | G | E | K |
| pmol | 168 | 154 | 154 | nd (40) | 131 | 134 | 128 | 126 | 118 (45) | 106 | 102 | 106 |
| Amino acid IIIb | N | Q | C | V | T | G | E | G | T | P | K | P |
| pmol | 106 | 95 (50) | nd | 87 | 82 | 80 | 74 (55) | 75 | 71 | 61 | 55 | 52 (60) |
| Amino acid IIIb | Q | S | H | N | D | G | D | F | E | E | I | P |
| pmol | 48 | 12 | 36 | 31 | 30 (65) | 24 | 21 | 23 | 18 | 16 | 18 | 12 |
| Amino acid | E | E | Y | L | Q | | | | | | | |

TABLE 15-continued

Quantitative sequence analysis of isohirudins IIIb and IIIb'

| IIIb | | | | | |
|---|---|---|---|---|---|
| pmol | 11 | 11 | 8 | 5 | 3 |

*amino acid exchange in comparison to (1)
**amino acid exchange in comparison to IIIb
nd: not determinable

We claim:
1. An Isohirudin comprising amino acids of a formula from the group:

A.
```
 1               5                    10
Val—Val—Tyr—Thr—Asp—Cys—Thr—Glu—Ser—Gly—
               15                    20
Gln—Asn—Leu—Cys—Leu—Cys—Glu—Gly—Ser—Asn—
               25                    30
Val—Cys—Gly—Lys—Gly—Asn—Lys—Cys—Ile—Leu—
               35                    40
Gly—Ser—Asp—Gly—Glu—Lys—Asn—Gln—Cys—Val—
               45                    50
Thr—Gly—Glu—Gly—Thr—Pro—Lys—Pro—Gln—Ser—
               55                    60
His—Asn—Asp—Gly—Asp—Phe—Glu—Glu—Ile—Pro—
                                     65
Glu—Glu—Tyr(R)—Leu—Gln
``` wherein R denotes hydrogen or $SO_3H$;

B.
```
 1               5                    10
Val—Val—Tyr—Thr—Asp—Cys—Thr—Glu—Ser—Gly—
               15                    20
Gln—Asn—Leu—Cys—Leu—Cys—Glu—Gly—Ser—Asn—
               25                    30
Val—Cys—Gly—Asn—Gly—Asn—Lys—Cys—Ile—Leu—
               35                    40
Gly—Ser—Asp—Gly—Glu—Lys—Asn—Gln—Cys—Val—
               45                    50
Thr—Gly—Glu—Gly—Thr—Pro—Lys—Pro—Gln—Ser—
               55                    60
His—Asn—Asp—Gly—Asp—Phe—Glu—Glu—Ile—Pro—
                                     65
Glu—Glu—Tyr(R)—Leu—Gln
``` wherein R denotes hydrogen or $SO_3H$;

C.
```
 1               5                    10
Ile—Thr—Tyr—Thr—Asp—Cys—Thr—Glu—Ser—Gly—
               15                    20
Gln—Asn—Leu—Cys—Leu—Cys—Glu—Gly—Ser—Asn—
               25                    30
Val—Cys—Gly—Asn—Gly—Asn—Lys—Cys—Lys—Leu—
               35                    40
Gly—Ser—Asp—Gly—Glu—Glu—Asn—Gln—Cys—Val—
               45                    50
Thr—Gly—Glu—Gly—Thr—Pro—Lys—Pro—Gln—Ser—
               55                    60
His—Asn—Asp—Gly—Asp—Phe—Glu—Glu—Ile—Pro—
                                     65
Glu—Glu—Tyr(R)—Leu—Gln
``` wherein R denotes hydrogen or $SO_3H$;

D.
```
 1               5                    10
Ile—Thr—Tyr—Thr—Asp—Cys—Thr—Glu—Ser—Gly—
               15                    20
Gln—Asp—Leu—Cys—Leu—Cys—Glu—Gly—Ser—Asn—
               25                    30
Val—Cys—Gly—Lys—Gly—Asn—Lys—Cys—Ile—Leu—
               35                    40
Gly—Ser—Asn—Gly—Glu—Glu—Asn—Gln—Cys—Val—
               45                    50
Thr—Gly—Glu—Gly—Thr—Pro—Lys—Pro—Gln—Ser—
               55                    60
His—Asn—Asp—Gly—Asp—Phe—Glu—Glu—Ile—Pro—
                                     65
Glu—Glu—Tyr(R)—Leu—Gln
``` wherein R denotes hydrogen or $SO_3H$;

E.
```
 1               5                    10
Ile—Thr—Tyr—Thr—Asp—Cys—Thr—Glu—Ser—Gly—
               15                    20
Gln—Asp—Leu—Cys—Leu—Cys—Glu—Gly—Ser—Asp—
               25                    30
Val—Cys—Gly—Lys—Gly—Asn—Lys—Cys—Ile—Leu—
               35                    40
Gly—Ser—Asn—Gly—Glu—Glu—Asn—Gln—Cys—Val—
               45                    50
Thr—Gly—Glu—Gly—Thr—Pro—Lys—Pro—Gln—Ser—
               55                    60
His—Asn—Asp—Gly—Asp—Phe—Glu—Glu—Ile—Pro—
                                     65
Glu—Glu—Tyr(R)—Leu—Gln
``` wherein R denotes hydrogen or $SO_3H$;

F.
```
 1               5                    10
Ile—Thr—Tyr—Thr—Asp—Cys—Thr—Glu—Ser—Gly—
               15                    20
Gln—Asn—Leu—Cys—Leu—Cys—Glu—Gly—Ser—Asn—
               25                    30
Val—Cys—Gly—Lys—Gly—Asn—Lys—Cys—Ile—Leu—
               35                    40
Gly—Ser—Asn—Gly—Glu—Asn—Asn—Gln—Cys—Val—
               45                    50
Thr—Gly—Glu—Gly—Thr—Pro—Lys—Pro—Gln—Ser—
               55                    60
His—Asn—Asp—Gly—Asp—Phe—Glu—Glu—Ile—Pro—
```

```
                                           65
                       Glu—Glu—Tyr(R)—Leu—Gln
``` wherein R denotes hydrogen or SO₃H;

```
1              5                  10        G.
Val—Val—Tyr—Thr—Asp—Cys—Thr—Glu—Ser—Gly—

15                 20
Gln—Asn—Leu—Cys—Leu—Cys—Glu—Asp—Ser—Asn—

25                 30
Val—Cys—Gly—Glu—Gly—Asn—Lys—Cys—Ile—Leu—

35                 40
Gly—Ser—Asn—Gly—Glu—Lys—Asn—Gln—Cys—Val—

45                 50
Thr—Gly—Glu—Gly—Thr—Pro—Lys—Pro—Gln—Ser—

55                 60
His—Asn—Asp—Gly—Asp—Phe—Glu—Glu—Ile—Pro—

65
                       Glu—Glu—Tyr(R)—Leu—Gln
``` wherein R denotes hydrogen or SO₃H;

```
1              5                  10        H.
Val—Val—Tyr—Thr—Asp—Cys—Thr—Glu—Ser—Gly—

15                 20
Glu—Asp—Leu—Cys—Leu—Cys—Glu—Gly—Ser—Asn—

25                 30
Val—Cys—Gly—Glu—Gly—Asn—Lys—Cys—Ile—Leu—

35                 40
Gly—Ser—Asp—Gly—Glu—Lys—Asn—Gln—Cys—Val—

45                 50
Thr—Gly—Glu—Gly—Thr—Pro—Lys—Pro—Gln—Ser—

55                 60
His—Asn—Asp—Gly—Asp—Phe—Glu—Glu—Ile—Pro—

65
                       Glu—Glu—Tyr(R)—Leu—Gln
``` wherein R denotes hydrogen or SO₃H;

```
1              5                  10        I.
Val—Val—Tyr—Thr—Asp—Cys—Thr—Glu—Ser—Gly—

15                 20
Gln—Asn—Leu—Cys—Leu—Cys—Glu—Asp—Ser—Asn—

25                 30
Val—Cys—Gly—Gln—Gly—Asn—Lys—Cys—Ile—Leu—

35                 40
Gly—Ser—Asn—Gly—Glu—Lys—Asn—Gln—Cys—Val—

45                 50
Thr—Gly—Glu—Gly—Thr—Pro—Lys—Pro—Gln—Ser—

55                 60
His—Asn—Asp—Gly—Asp—Phe—Glu—Glu—Ile—Pro—

65
                       Glu—Glu—Tyr(R)—Leu—Gln
``` wherein R denotes hydrogen or SO₃H;

```
1              5                  10        J.
Val—Val—Tyr—Thr—Asp—Cys—Thr—Glu—Ser—Gly—

15                 20
Gln—Asn—Leu—Cys—Leu—Cys—Gln—Asp—Ser—Asn—

25                 30
Val—Cys—Gly—Gln—Gly—Asn—Lys—Cys—Ile—Leu—

35                 40
Gly—Ser—Asn—Gly—Glu—Lys—Asn—Gln—Cys—Val—

45                 50
Thr—Gly—Glu—Gly—Thr—Pro—Lys—Pro—Gln—Ser—

55                 60
His—Asn—Asp—Gly—Asp—Phe—Glu—Glu—Ile—Pro—

65
                       Glu—Glu—Tyr(R)—Leu—Gln
``` wherein R denotes hydrogen or SO₃H; and

```
1              5                  10        K.
Val—Val—Tyr—Thr—Asp—Cys—Thr—Glu—Ser—Gly—

15                 20
Gln—Asn—Leu—Cys—Leu—Cys—Gln—Gly—Ser—Asn—

25                 30
Val—Cys—Gly—Gln—Gly—Asn—Lys—Cys—Ile—Leu—

35                 40
Gly—Ser—Asn—Gly—Glu—Lys—Asn—Gln—Cys—Val—

45                 50
Thr—Gly—Glu—Gly—Thr—Pro—Lys—Pro—Gln—Ser—

55                 60
His—Asn—Asp—Gly—Asp—Phe—Glu—Glu—Ile—Pro—

65
                       Glu—Glu—Tyr(R)—Leu—Gln
``` wherein R denotes hydrogen or SO₃H.

2. An Isohirudin as claimed in claim 1, wherein the formula is:

```
1              5                  10
Val—Val—Tyr—Thr—Asp—Cys—Thr—Glu—Ser—Gly—

15                 20
Gln—Asn—Leu—Cys—Leu—Cys—Glu—Gly—Ser—Asn—

25                 30
Val—Cys—Gly—Lys—Gly—Asn—Lys—Cys—Ile—Leu—

35                 40
Gly—Ser—Asp—Gly—Glu—Lys—Asn—Gln—Cys—Val—

45                 50
Thr—Gly—Glu—Gly—Thr—Pro—Lys—Pro—Gln—Ser—

55                 60
His—Asn—Asp—Gly—Asp—Phe—Glu—Glu—Ile—Pro—

65
                       Glu—Glu—Tyr(R)—Leu—Gln
``` wherein R denotes hydrogen or SO₃H.

3. An Isohirudin as claimed in claim 1, wherein the formula is:

```
1              5                  10
Val—Val—Tyr—Thr—Asp—Cys—Thr—Glu—Ser—Gly—

15                 20
Gln—Asn—Leu—Cys—Leu—Cys—Glu—Gly—Ser—Asn—
```

-continued
```
              25                            30
Val—Cys—Gly—Asn—Gly—Asn—Lys—Cys—Ile—Leu—

35                            40
Gly—Ser—Asp—Gly—Glu—Lys—Asn—Gln—Cys—Val—

45                            50
Thr—Gly—Glu—Gly—Thr—Pro—Lys—Pro—Gln—Ser—

55                            60
His—Asn—Asp—Gly—Asp—Phe—Glu—Glu—Ile—Pro—

65
                        Glu—Glu—Tyr(R)—Leu—Gln
``` wherein R denotes hydrogen or SO$_3$H.

4. An Isohirudin as claimed in claim 1, wherein the formula is:

```
  1              5                          10
Ile—Thr—Tyr—Thr—Asp—Cys—Thr—Glu—Ser—Gly—

15                            20
Gln—Asn—Leu—Cys—Leu—Cys—Glu—Gly—Ser—Asn—

25                            30
Val—Cys—Gly—Asn—Gly—Asn—Lys—Cys—Lys—Leu—

35                            40
Gly—Ser—Asp—Gly—Glu—Glu—Asn—Gln—Cys—Val—

45                            50
Thr—Gly—Glu—Gly—Thr—Pro—Lys—Pro—Gln—Ser—

55                            60
His—Asn—Asp—Gly—Asp—Phe—Glu—Glu—Ile—Pro—

65
                        Glu—Glu—Tyr(R)—Leu—Gln
``` wherein R denotes hydrogen or SO$_3$H.

5. An Isohirudin as claimed in claim 1, wherein the formula is:

```
  1              5                          10
Ile—Thr—Tyr—Thr—Asp—Cys—Thr—Glu—Ser—Gly—

15                            20
Gln—Asp—Leu—Cys—Leu—Cys—Glu—Gly—Ser—Asn—

25                            30
Val—Cys—Gly—Lys—Gly—Asn—Lys—Cys—Ile—Leu—

35                            40
Gly—Ser—Asn—Gly—Glu—Glu—Asn—Gln—Cys—Val—

45                            50
Thr—Gly—Glu—Gly—Thr—Pro—Lys—Pro—Gln—Ser—

55                            60
His—Asn—Asp—Gly—Asp—Phe—Glu—Glu—Ile—Pro—

65
                        Glu—Glu—Tyr(R)—Leu—Gln
``` wherein R denotes hydrogen or SO$_3$H.

6. An Isohirudin as claimed in claim 1, wherein the formula is:

```
  1              5                          10
Ile—Thr—Tyr—Thr—Asp—Cys—Thr—Glu—Ser—Gly—

15                            20
Gln—Asp—Leu—Cys—Leu—Cys—Glu—Gly—Ser—Asp—

25                            30
Val—Cys—Gly—Lys—Gly—Asn—Lys—Cys—Ile—Leu—

35                            40
Gly—Ser—Asn—Gly—Glu—Glu—Asn—Gln—Cys—Val—

45                            50
Thr—Gly—Glu—Gly—Thr—Pro—Lys—Pro—Gln—Ser—

55                            60
His—Asn—Asp—Gly—Asp—Phe—Glu—Glu—Ile—Pro—

65
                        Glu—Glu—Tyr(R)—Leu—Gln
``` wherein R denotes hydrogen or SO$_3$H.

7. An Isohirudin as claimed in claim 1, wherein the formula is:

```
  1              5                          10
Ile—Thr—Tyr—Thr—Asp—Cys—Thr—Glu—Ser—Gly—

15                            20
Gln—Asn—Leu—Cys—Leu—Cys—Glu—Gly—Ser—Asn—

25                            30
Val—Cys—Gly—Lys—Gly—Asn—Lys—Cys—Ile—Leu—

35                            40
Gly—Ser—Asn—Gly—Glu—Glu—Asn—Gln—Cys—Val—

45                            50
Thr—Gly—Glu—Gly—Thr—Pro—Lys—Pro—Gln—Ser—

55                            60
His—Asn—Asp—Gly—Asp—Phe—Glu—Glu—Ile—Pro—

65
                        Glu—Glu—Tyr(R)—Leu—Gln
``` wherein R denotes hydrogen or SO$_3$H.

8. An Isohirudin as claimed in claim 1, wherein the formula is:

```
  1              5                          10
Val—Val—Tyr—Thr—Asp—Cys—Thr—Glu—Ser—Gly—

15                            20
Gln—Asn—Leu—Cys—Leu—Cys—Glu—Asp—Ser—Asn—

25                            30
Val—Cys—Gly—Glu—Gly—Asn—Lys—Cys—Ile—Leu—

35                            40
Gly—Ser—Asn—Gly—Glu—Lys—Asn—Gln—Cys—Val—

45                            50
Thr—Gly—Glu—Gly—Thr—Pro—Lys—Pro—Gln—Ser—

55                            60
His—Asn—Asp—Gly—Asp—Phe—Glu—Glu—Ile—Pro—

65
                        Glu—Glu—Tyr(R)—Leu—Gln
``` wherein R denotes hydrogen or SO$_3$H.

9. An Isohirudin as claimed in claim 1, wherein the formula is:

```
  1              5                          10
Val—Val—Tyr—Thr—Asp—Cys—Thr—Glu—Ser—Gly—

15                            20
Glu—Asp—Leu—Cys—Leu—Cys—Glu—Gly—Ser—Asn—

25                            30
Val—Cys—Gly—Glu—Gly—Asn—Lys—Cys—Ile—Leu—
```

-continued

```
                35                    40
     Gly—Ser—Asp—Gly—Glu—Lys—Asn—Glu—Cys—Val—
                45                    50
     Thr—Gly—Glu—Gly—Thr—Pro—Lys—Pro—Gln—Ser—
                55                    60
     His—Asn—Asp—Gly—Asp—Phe—Glu—Glu—Ile—Pro—
                                         65
                           Glu—Glu—Tyr(R)—Leu—Gln
``` wherein R denotes hydrogen or SO₃H.

10. An Isohirudin as claimed in claim 1, wherein the formula is:

```
     1              5                   10
     Val—Val—Tyr—Thr—Asp—Cys—Thr—Glu—Ser—Gly—
                15                    20
     Gln—Asn—Leu—Cys—Leu—Cys—Glu—Asp—Ser—Asn—
                25                    30
     Val—Cys—Gly—Gln—Gly—Asn—Lys—Cys—Ile—Leu—
                35                    40
     Gly—Ser—Asn—Gly—Glu—Lys—Asn—Gln—Cys—Val—
                45                    50
     Thr—Gly—Glu—Gly—Thr—Pro—Lys—Pro—Gln—Ser—
                55                    60
     His—Asn—Asp—Gly—Asp—Phe—Glu—Glu—Ile—Pro—
                                         65
                           Glu—Glu—Tyr(R)—Leu—Gln
``` wherein R denotes hydrogen or SO₃H.

11. An Isohirudin as claimed in claim 1, wherein the formula is:

```
     1              5                   10
     Val—Val—Tyr—Thr—Asp—Cys—Thr—Glu—Ser—Gly—
                15                    20
     Gln—Asn—Leu—Cys—Leu—Cys—Gln—Asp—Ser—Asn—
                25                    30
     Val—Cys—Gly—Gln—Gly—Asn—Lys—Cys—Ile—Leu—
                35                    40
     Gly—Ser—Asn—Gly—Glu—Lys—Asn—Gln—Cys—Val—
                45                    50
     Thr—Gly—Glu—Gly—Thr—Pro—Lys—Pro—Gln—Ser—
                55                    60
     His—Asn—Asp—Gly—Asp—Phe—Glu—Glu—Ile—Pro—
                                         65
                           Glu—Glu—Tyr(R)—Leu—Gln
``` wherein R denotes hydrogen or SO₃H.

12. An Isohirudin as claimed in claim 1, wherein the formula is:

```
     1              5                   10
     Val—Val—Tyr—Thr—Asp—Cys—Thr—Glu—Ser—Gly—
                15                    20
     Gln—Asn—Leu—Cys—Leu—Cys—Gln—Gly—Ser—Asn—
                25                    30
     Val—Cys—Gly—Gln—Gly—Asn—Lys—Cys—Ile—Leu—
                35                    40
     Gly—Ser—Asn—Gly—Glu—Lys—Asn—Gln—Cys—Val—
                45                    50
     Thr—Gly—Glu—Gly—Thr—Pro—Lys—Pro—Gln—Ser—
                55                    60
     His—Asn—Asp—Gly—Asp—Phe—Glu—Glu—Ile—Pro—
                                         65
                           Glu—Glu—Tyr(R)—Leu—Gln
``` wherein R denotes hydrogen or SO₃H.

* * * * *